(12) United States Patent
Murphy

(10) Patent No.: US 10,918,835 B2
(45) Date of Patent: Feb. 16, 2021

(54) DELIVERY SYSTEM FOR ACTIVE AGENT COATED BALLOON

(71) Applicant: Surmodics, Inc., Eden Prairie, MN (US)

(72) Inventor: Rick Murphy, White Bear Lake, MN (US)

(73) Assignee: Surmodics, Inc., Eden Prairie, MN (US)

( * ) Notice: Subject to any disclaimer, the term of this patent is extended or adjusted under 35 U.S.C. 154(b) by 685 days.

(21) Appl. No.: 15/467,530

(22) Filed: Mar. 23, 2017

(65) Prior Publication Data

US 2017/0281913 A1 Oct. 5, 2017

Related U.S. Application Data

(60) Provisional application No. 62/315,788, filed on Mar. 31, 2016.

(51) Int. Cl.
*A61M 25/01* (2006.01)
*A61L 29/08* (2006.01)
(Continued)

(52) U.S. Cl.
CPC ....... *A61M 25/0194* (2013.01); *A61L 29/041* (2013.01); *A61L 29/049* (2013.01);
(Continued)

(58) Field of Classification Search
CPC ...... A61M 25/0194; A61M 2025/0681; A61M 2025/1088; A61M 2025/1079;
(Continued)

(56) References Cited

U.S. PATENT DOCUMENTS

| 4,195,637 A | 4/1980 | Gruntzig et al. |
| 4,973,993 A | 11/1990 | Allen |

(Continued)

FOREIGN PATENT DOCUMENTS

| CN | 1056430 | 11/1991 |
| CN | 101048188 | 10/2007 |

(Continued)

OTHER PUBLICATIONS

"International Preliminary Report on Patentability," for PCT Application No. PCT/US2016/050703 dated Mar. 29, 2018 (9 pages).

(Continued)

*Primary Examiner* — Jenna Zhang
(74) *Attorney, Agent, or Firm* — Pauly, DeVries Smith & Deffner LLC

(57) ABSTRACT

Embodiments herein include delivery systems for active agent coated balloons and related methods. In an embodiment, a delivery system can include a tunneling sheath and a balloon catheter. The tunneling sheath can include a tubular shaft having an outer diameter and defining a lumen. The tunneling sheath can include a proximal collar defining a lumen. The balloon catheter can include a balloon catheter shaft disposed within the tubular shaft. The balloon catheter shaft can include a lumen for the passage of a fluid therein. The balloon catheter can include an expandable balloon disposed on the balloon catheter shaft. The balloon catheter shaft can include an active agent layer disposed on the expandable balloon. The position of the expandable balloon can be configured to be stationary relative to the tubular shaft as the delivery system is passed through a blood vessel of a patient. Other embodiments are also included herein.

17 Claims, 8 Drawing Sheets

(51) Int. Cl.
  *A61M 25/10* (2013.01)
  *A61L 29/04* (2006.01)
  *A61L 29/06* (2006.01)
  *A61L 29/14* (2006.01)
  *A61L 29/16* (2006.01)
  *A61L 29/18* (2006.01)
  *A61M 25/06* (2006.01)
  *A61M 25/00* (2006.01)

(52) U.S. Cl.
  CPC ............. *A61L 29/06* (2013.01); *A61L 29/08* (2013.01); *A61L 29/085* (2013.01); *A61L 29/14* (2013.01); *A61L 29/16* (2013.01); *A61L 29/18* (2013.01); *A61M 25/10* (2013.01); *A61L 2300/416* (2013.01); *A61L 2400/10* (2013.01); *A61M 25/007* (2013.01); *A61M 2025/0681* (2013.01); *A61M 2025/105* (2013.01); *A61M 2025/1075* (2013.01); *A61M 2025/1079* (2013.01); *A61M 2025/1081* (2013.01); *A61M 2025/1088* (2013.01); *A61M 2025/1093* (2013.01)

(58) Field of Classification Search
  CPC .. A61M 2025/1075; A61M 2025/1081; A61M 2025/105; A61M 25/10
  See application file for complete search history.

(56) References Cited

U.S. PATENT DOCUMENTS

| | | | |
|---|---|---|---|
| 5,041,089 | A | 8/1991 | Mueller et al. |
| 5,087,246 | A | 2/1992 | Smith |
| 5,254,107 | A * | 10/1993 | Soltesz ............... A61M 25/005 138/125 |
| 5,318,587 | A | 6/1994 | Davey |
| 5,382,234 | A | 1/1995 | Cornelius et al. |
| 5,414,075 | A | 5/1995 | Swan et al. |
| 5,571,089 | A | 11/1996 | Crocker |
| 5,582,165 | A | 12/1996 | Bryan et al. |
| 5,637,460 | A | 6/1997 | Swan et al. |
| 5,714,360 | A | 2/1998 | Swan et al. |
| 5,776,101 | A | 7/1998 | Goy |
| 5,807,331 | A | 9/1998 | Den Heijer et al. |
| 5,858,653 | A | 1/1999 | Duran et al. |
| 5,876,374 | A | 3/1999 | Alba et al. |
| 5,882,336 | A | 3/1999 | Janacek |
| 6,007,833 | A | 12/1999 | Chudzik et al. |
| 6,077,698 | A | 6/2000 | Swan et al. |
| 6,156,016 | A | 12/2000 | Maginot |
| 6,190,371 | B1 | 2/2001 | Maginot et al. |
| 6,278,018 | B1 | 8/2001 | Swan |
| 6,394,995 | B1 | 5/2002 | Solar et al. |
| 6,465,178 | B2 | 10/2002 | Chappa et al. |
| 6,514,734 | B1 | 2/2003 | Clapper et al. |
| 6,517,515 | B1 | 2/2003 | Eidenschink |
| 6,537,254 | B1 | 3/2003 | Schock et al. |
| 6,603,040 | B1 | 8/2003 | Swan |
| 6,623,504 | B2 | 9/2003 | Vrba et al. |
| 6,762,019 | B2 | 7/2004 | Swan et al. |
| 6,896,842 | B1 | 5/2005 | Hamilton et al. |
| 7,138,541 | B2 | 11/2006 | Swan |
| 7,163,523 | B2 | 1/2007 | Devens, Jr. et al. |
| 7,309,593 | B2 | 12/2007 | Ofstead et al. |
| 7,348,055 | B2 | 3/2008 | Chappa et al. |
| 7,736,689 | B2 | 6/2010 | Chappa et al. |
| 7,772,393 | B2 | 8/2010 | Guire et al. |
| 7,807,750 | B2 | 10/2010 | Taton et al. |
| 8,039,524 | B2 | 10/2011 | Ralph et al. |
| 8,487,137 | B2 | 7/2013 | Guire et al. |
| 8,513,320 | B2 | 8/2013 | Rooijmans |
| 8,679,063 | B2 | 3/2014 | Stout et al. |
| 8,809,411 | B2 | 8/2014 | Rooijmans |
| 8,889,760 | B2 | 11/2014 | Kurdyumov et al. |
| 10,478,546 | B2 | 11/2019 | Slager et al. |
| 2005/0059925 | A1 | 3/2005 | Maginot et al. |
| 2007/0032882 | A1 | 2/2007 | Lodhi et al. |
| 2008/0125750 | A1 | 5/2008 | Gaissert |
| 2010/0198168 | A1 | 8/2010 | Rooijmans |
| 2010/0228333 | A1 * | 9/2010 | Drasler ............... A61L 29/10 623/1.11 |
| 2010/0274012 | A1 | 10/2010 | Guire et al. |
| 2011/0106014 | A1 | 5/2011 | Helm, Jr. |
| 2011/0144373 | A1 | 6/2011 | Swan et al. |
| 2012/0148852 | A1 | 6/2012 | Jelle et al. |
| 2012/0149934 | A1 | 6/2012 | Kurdyumov |
| 2012/0221024 | A1 | 8/2012 | Sutton et al. |
| 2012/0274012 | A1 | 11/2012 | Guenther et al. |
| 2012/0296313 | A1 * | 11/2012 | Andreacchi ....... A61M 25/0668 604/509 |
| 2013/0143056 | A1 | 6/2013 | Swan et al. |
| 2013/0237950 | A1 * | 9/2013 | Gianotti ................ A61F 2/958 604/500 |
| 2013/0302529 | A1 | 11/2013 | Kurdyumov |
| 2014/0025044 | A1 * | 1/2014 | Zamarripa ........ A61M 25/0097 604/533 |
| 2015/0190618 | A1 | 7/2015 | Kantor |
| 2017/0072129 | A1 | 3/2017 | Slager et al. |

FOREIGN PATENT DOCUMENTS

| | | |
|---|---|---|
| CN | 101219242 | 7/2008 |
| CN | 201683986 | 12/2010 |
| CN | 103476450 | 12/2013 |
| WO | 2008039910 | 4/2008 |
| WO | 2014186729 | 11/2014 |
| WO | 2015077545 | 5/2015 |
| WO | 2017048576 | 3/2017 |
| WO | 2017172607 | 10/2017 |

OTHER PUBLICATIONS

"International Search Report and Written Opinion," for PCT Application No. PCT/US2017/024286 dated Jul. 5, 2017 (19 pages).
"International Preliminary Report on Patentability," for PCT Application No. PCT/US2017/024286 dated Oct. 11, 2018 (12 pages).
"Non-Final Office Action," for U.S. Appl. No. 15/257,252 dated Feb. 19, 2019 (30 pages).
"Response to Communication Pursuant to Rules 161(1) and 162 EPC," for European Patent Application No. 16770135.8 filed with the EPO on Oct. 24, 2018 (7 pages).
"International Search Report and Written Opinion," for PCT application No. PCT/US2016/050703 dated Dec. 16, 2016 (14 pages).
Love, Kevin T. et al., "Lipid-like materials for low-dose, in vivo gene silencing," PNAS 107: 1864-1869 (2010) (7 pages).
"Notice of Allowance," for U.S. Appl. No. 15/257,252 dated Jul. 2, 2019 (9 pages).
"Response to Communication Pursuant to Rules 161(1) and 162 EPC," for European Patent Application No. 17715380.6 filed May 2, 2019 (20 pages).
"Response to Non-Final Rejection," dated Feb. 19, 2019 for U.S. Appl. No. 15/275,252, submitted via EFS-Web on May 17, 2019, 10 pages.
"First Office Action," for Chinese Patent Application No. 2016800647381 dated Mar. 25, 2020 (27 pages) with English Translation.

* cited by examiner

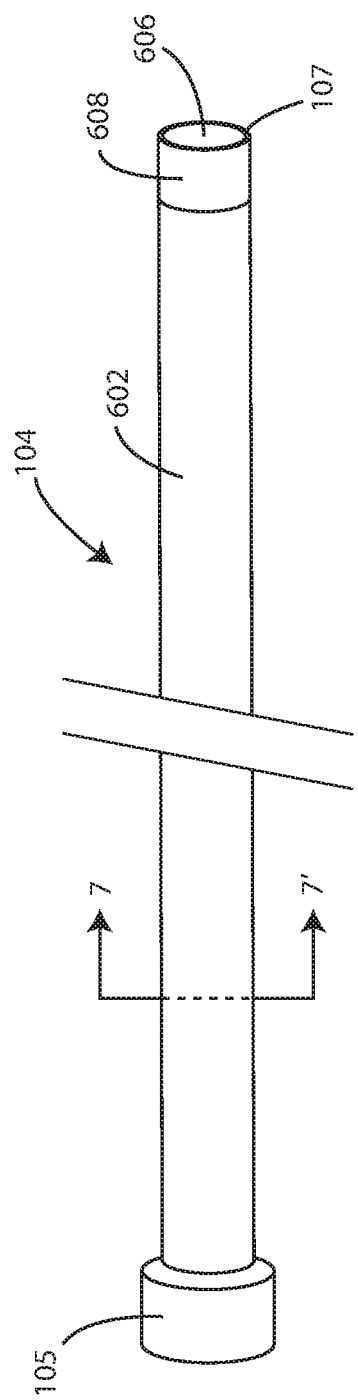
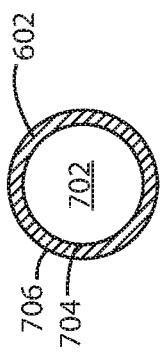
FIG. 6
FIG. 7

DELIVERY SYSTEM FOR ACTIVE AGENT COATED BALLOON

This application claims the benefit of U.S. Provisional Application No. 62/315,788, filed Mar. 31, 2016, the contents of which are herein incorporated by reference.

FIELD

Embodiments herein relate to delivery systems for active agent coated balloons and related methods.

BACKGROUND

The vascular system of the human is subject to blockage due to plaque within the arteries. Partial and even complete blockage of arteries by the formation of an atherosclerotic plaque is a well-known and frequent medical problem. Frequently, such blockage occurs in the coronary arteries. Blockages may also occur secondary to past treatment of specific sites (restenosis—such as that stemming from rapidly dividing smooth muscle cells). In addition, blockages can also occur in the context of peripheral arteries.

One common procedure for the treatment of blocked arteries is percutaneous transluminal coronary angioplasty (PTCA), also referred to as balloon angioplasty. In this procedure, a catheter having an inflatable balloon at its distal end is introduced into the coronary artery, the deflated, folded balloon is positioned at the stenotic site (or target lesion), and then the balloon is inflated. Inflation of the balloon disrupts and flattens the plaque against the arterial wall, and stretches the arterial wall, resulting in enlargement of the intraluminal passageway and increased blood flow. After such expansion, the balloon is deflated, and the balloon catheter removed. A similar procedure, called percutaneous transluminal angioplasty (PTA), is used in arteries other than coronary arteries in the vascular system.

During such procedures, it may be desirable to deliver a therapeutic agent or drug to the area where the treatment is occurring. Such active agents can be disposed onto the balloon and then transferred to the tissue site or target lesion when the balloon is expanded.

Similarly, it may be useful to deliver active agents from expandable balloons for entirely different procedures. Additionally, it may be desirable to transfer therapeutic agents to other locations in a mammal, such as the skin, neurovasculature, nasal, oral, the lungs, the mucosa, sinus, the GI tract or the renal peripheral vasculature. This can also be accomplished through the use of an active agent coated balloon.

SUMMARY

Embodiments herein include delivery systems for active agent coated balloons and related methods. In an embodiment, a delivery system for introducing an active agent coated balloon into a subject is included. The delivery system can include a tunneling sheath. The tunneling sheath can include a tubular shaft having an outer diameter and defining a lumen, the shaft having a proximal end and a distal end. The tunneling sheath can include a proximal collar defining a lumen. The proximal collar can be attached to the tubular shaft at the proximal end. The proximal collar can have an outer diameter that is greater than the outer diameter of the tubular shaft. The delivery system can further include a balloon catheter. The balloon catheter can include a balloon catheter shaft disposed within the tubular shaft. The balloon catheter shaft can include a lumen for the passage of a fluid therein. The balloon catheter can include an expandable balloon disposed on the balloon catheter shaft in fluid communication with the lumen of the balloon catheter shaft. The balloon catheter shaft can include an active agent layer disposed on the expandable balloon. The position of the expandable balloon can be configured to be stationary relative to the tubular shaft as the delivery system is passed through a blood vessel of a patient.

In an embodiment, a method of delivering an active agent coated balloon into a subject is included. The method can include inserting a delivery system for introducing an active agent coated balloon into a subject. The method can further include advancing the delivery system through a blood vessel of the subject so as to be adjacent the site of an area to be treated, wherein the position of the expandable balloon is stationary relative to the tubular shaft as the delivery system is advanced through the blood vessel of the patient. The method can further include advancing the balloon catheter shaft and the expandable balloon out of the tubular shaft. The method can further include inflating the expandable balloon so that it contacts the area to be treated.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which:

FIG. 6 is a schematic view of a tunneling sheath in accordance with various embodiments herein.

FIG. 7 is a schematic cross-sectional view of a tunneling sheath as taken along line 7-7' of FIG. 6.

Figure 1:
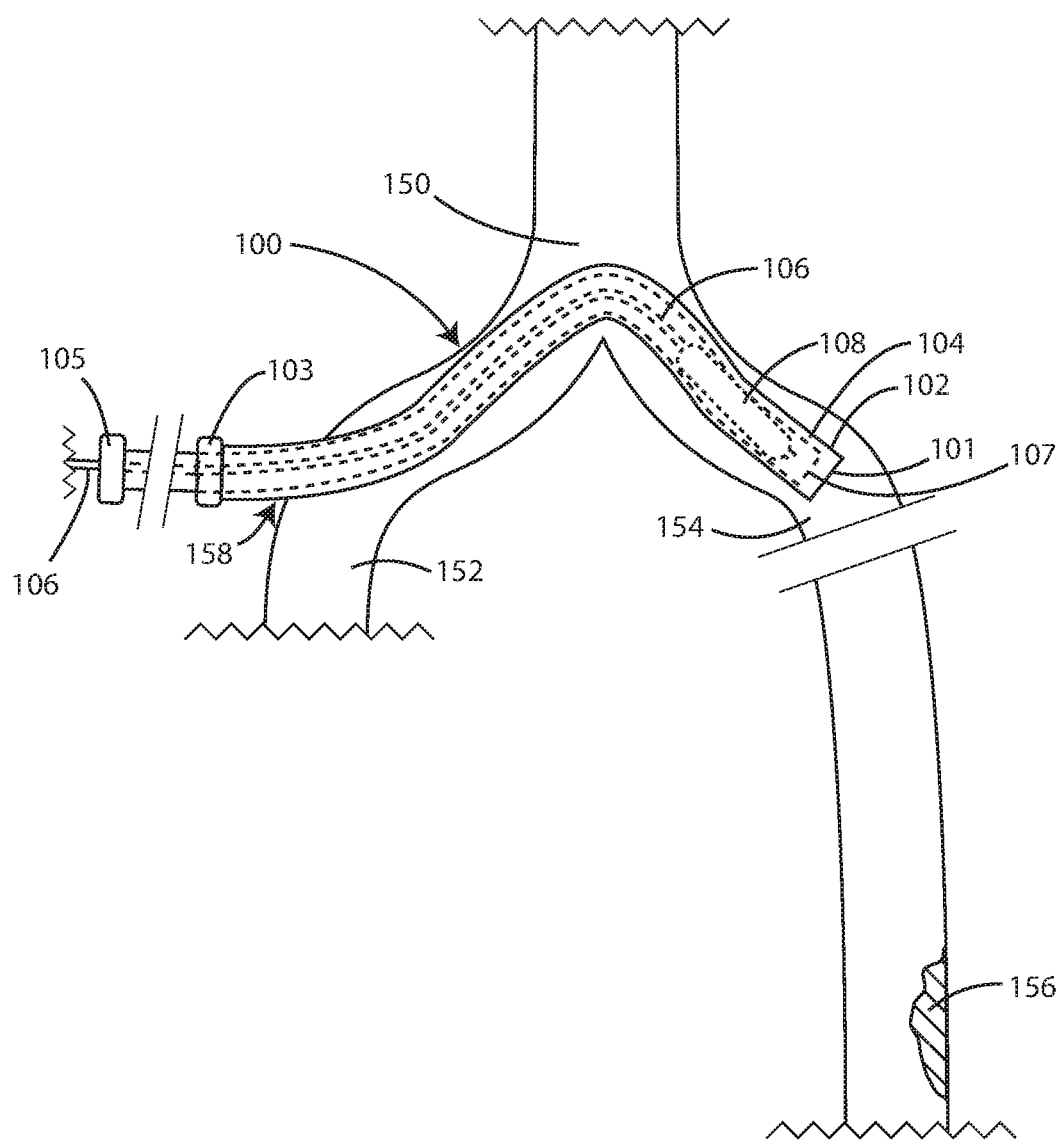
FIG. 1 is a schematic view of a delivery system in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

The embodiments described herein are not intended to be exhaustive or to limit the invention to the precise forms disclosed in the following detailed description. Rather, the embodiments are chosen and described so that others skilled in the art can appreciate and understand the principles and practices.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As described above, one useful approach to delivering an active agent to a target site or target lesion is to dispose the active agent or drug onto an expandable balloon of a balloon catheter and then position the catheter appropriately and inflate the balloon. The active agent can be transferred from the balloon surface to the desired tissue site and/or move with the fluid in the vasculature into which the balloon was placed.

However, maximizing the amount of active agent that gets transferred to the target site can be challenging. During the procedure, the balloon can contact the surfaces of other medical components and a certain amount of the active agent can be lost through such contact. In addition, the surfaces of the active agent coating can sometimes be damaged.

In accordance with embodiments herein, a delivery system for introducing an active agent coated balloon into a subject is included. The delivery system can include a tunneling sheath and a balloon catheter. The position of the expandable balloon can be configured to be stationary relative to the tubular shaft as the delivery system is passed through a blood vessel of a patient. As such the tunneling sheath can act as a balloon protector during clinician handing of the device. The balloon can stay dry and the active agent coating on the balloon can avoid contact with moisture, blood, etc. during the procedure preparation stage of the operation. Further, the tunneling sheath can protect the active agent coated balloon during introduction of the delivery system through a hemostatic valve. Further, the tunneling sheath can prevent active agent loss during transport of the balloon through to a site to be treated. It is believed that 30 percent or more of the active agent can be lost while pushing a balloon catheter through a sheath. In addition, the tunneling sheath can assist in guiding the active agent coated balloon catheter through lesions. In addition, the tunneling sheath can aid in positioning of the active agent coated balloon catheter.

Referring now to FIG. 1, a schematic view is shown of a delivery system 100 in accordance with various embodiments herein. The delivery system 100 is shown passing through an access site 158 into a vessel 150 of a patient. The vessel 150 can include a first branch 152 and a second branch 154. The vessel 150 can include a target lesion 156 (or site to be treated). In some embodiments, the access site 158 can be in a first branch 152 of a vessel 150 that is contralateral from a second branch 154 that contains the target lesion 156.

The delivery system 100 can include a tunneling sheath 104 and a balloon catheter 106 disposed within the tunneling sheath 104. The tunneling sheath 104 has a distal end 107 and a proximal collar 105 (or hub). The balloon catheter 106 can pass through the proximal collar 105 and can have a balloon 108 disposed therein. In this view, the tunneling sheath 104 and the balloon catheter 106 are disposed within an introducing sheath 102. The introducing sheath 102 has a distal end 101 and a proximal collar 103.

In the view shown in FIG. 1, the delivery system 100 is within the vessel 150. Specifically, the delivery system 100 is within the introducing sheath 102. The tunneling sheath 104 and a balloon catheter 106 can move together through the introducing sheath 102. Specifically, the tunneling sheath 104 and a balloon catheter 106 can be fixed with respect to one another so that they move together. In some embodiments, the proximal collar 105 can be fastened onto the balloon catheter 106, such as through a twisting motion of the proximal collar 105 that can reduce the diameter of an aperture passing through the proximal collar 105.

Figure 2:
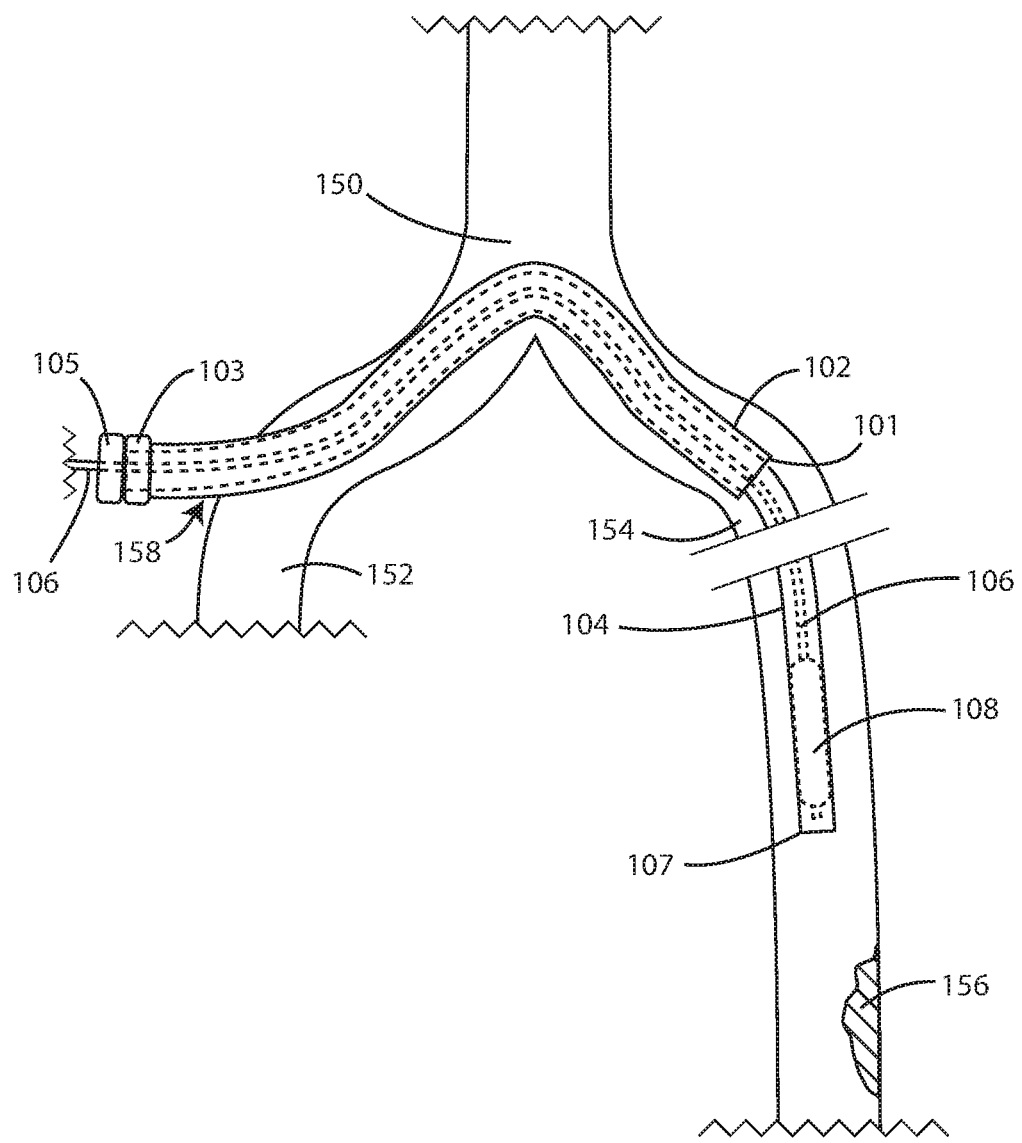
FIG. 2 is a schematic view of a delivery system in accordance with various embodiments herein.

Referring now to FIG. 2, a schematic view is shown of the delivery system 100 in accordance with various embodiments herein. In this view, the tunneling sheath 104 and the balloon catheter 106 have moved together through the introducing sheath 102 in order to get a closer approach to the target lesion 156. In specific, the distal end 107 of the tunneling sheath 104, and the balloon 108 therein, has passed out of the distal end 101 of the introducing sheath 102.

Figure 3:
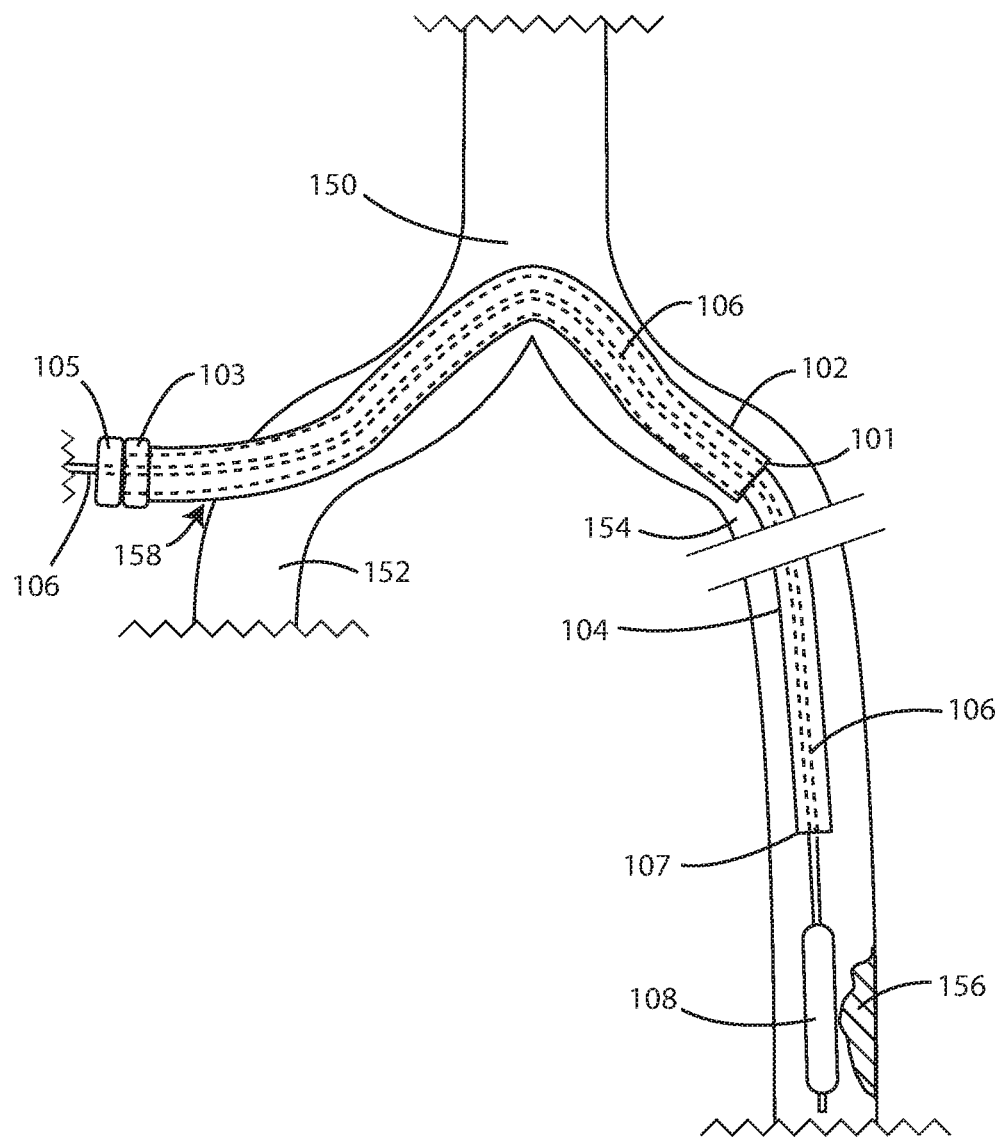
FIG. 3 is a schematic view of a delivery system in accordance with various embodiments herein.

Referring now to FIG. 3, a schematic view is shown of a delivery system in accordance with various embodiments herein. In this view, the balloon catheter 106 (and the balloon 108) have passed out of the distal end of the tunneling sheath 104. In specific, the balloon 108 has moved into a position adjacent the target lesion 156. If the proximal collar 105 was previously fastened onto the balloon catheter 106, then it is loosened other otherwise detached so that the balloon catheter 106 can move independently from the tunneling sheath 104.

Figure 4:
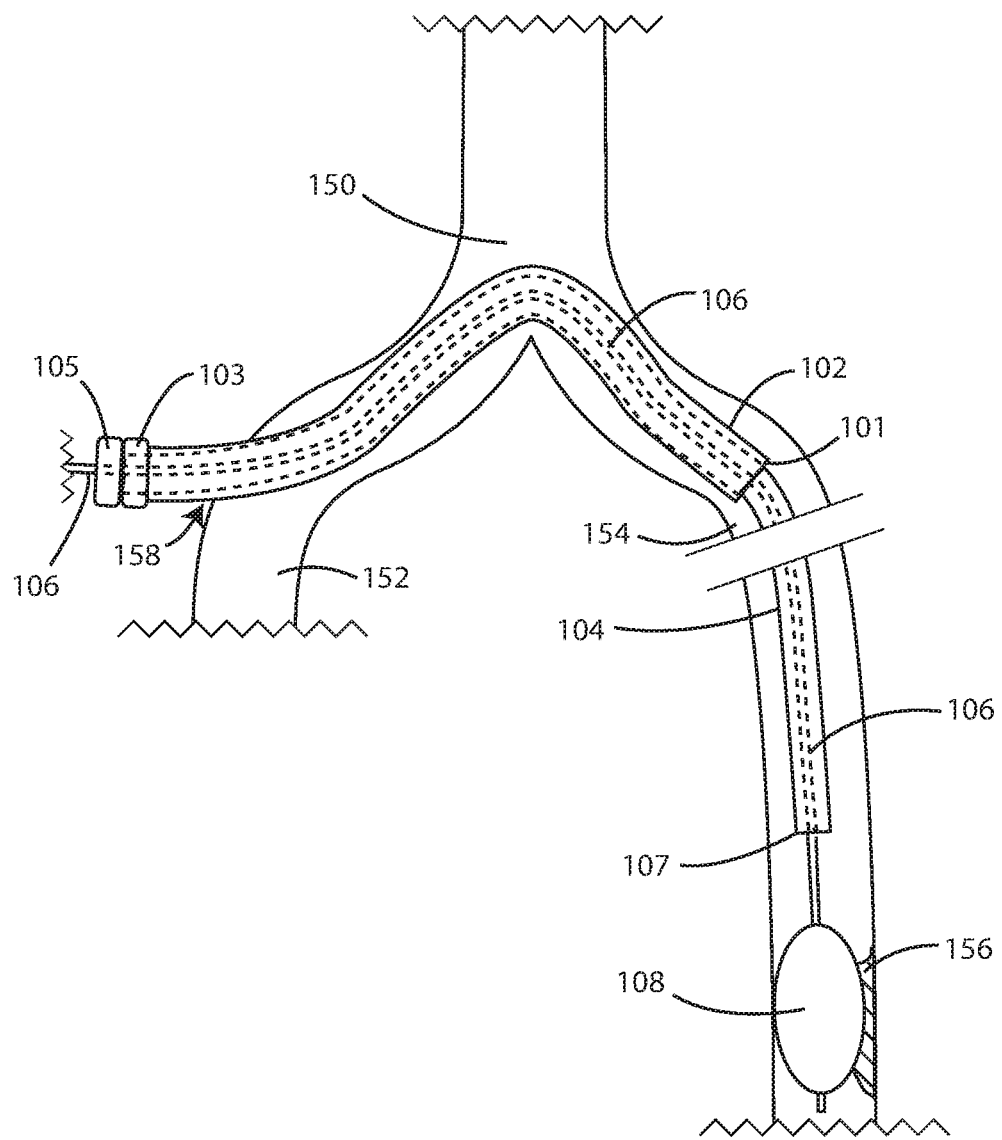
FIG. 4 is a schematic view of a delivery system in accordance with various embodiments herein.

Referring now to FIG. 4, a schematic view is shown of a delivery system 100 in accordance with various embodiments herein. In this view, the balloon 108 of the balloon catheter 106 has now been inflated in order to treat the target lesion 156. The balloon can include an active agent layer thereon including a bioactive agent (or active agent) for treating restenosis. The bioactive agent can be selected from the group consisting of paclitaxel, rapamycin and derivatives thereof. However, exemplary active agents are described in greater detail below.

Figure 5:
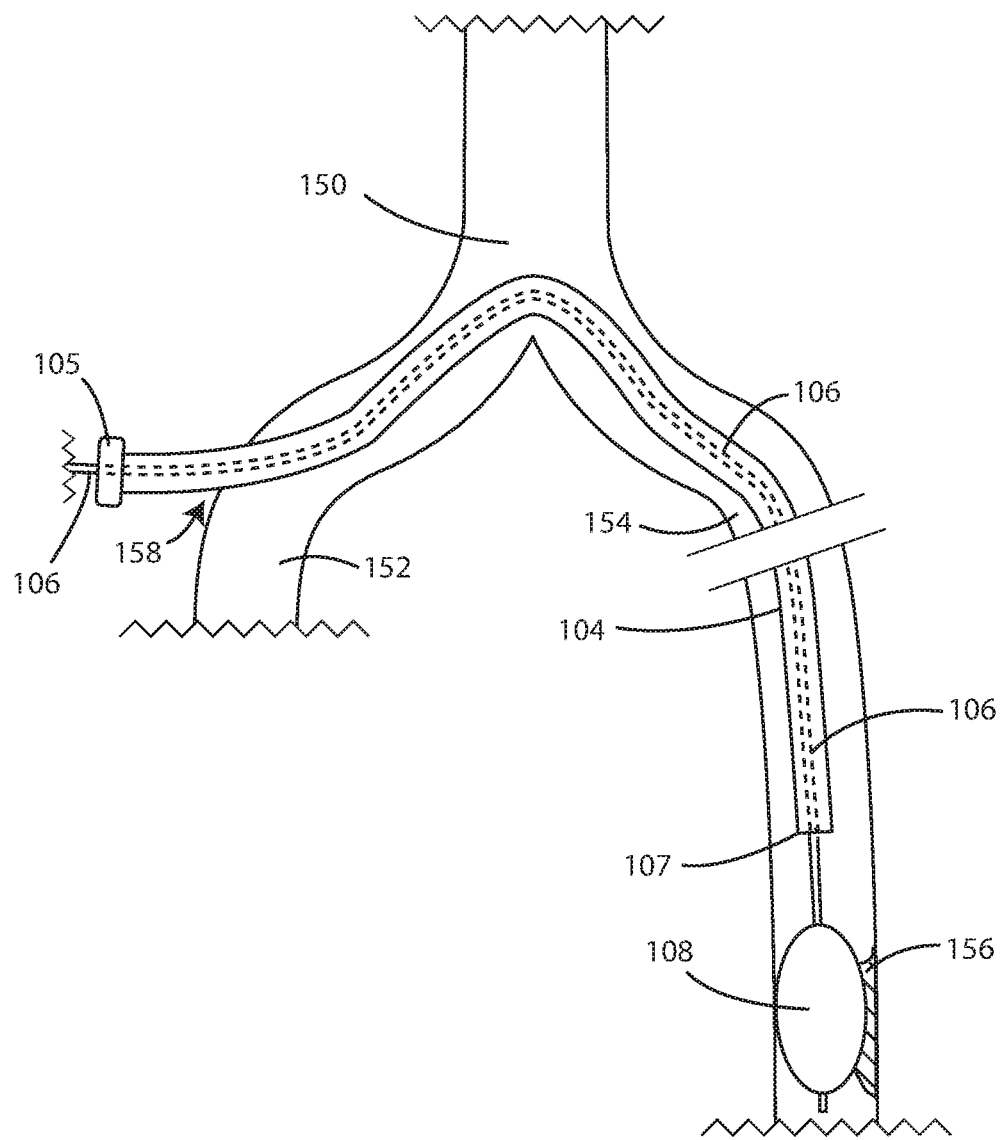
FIG. 5 is a schematic view of a delivery system in accordance with various embodiments herein.

It will be appreciated that in some embodiments an introducing sheath may be omitted. Referring now to FIG. 5, a schematic view is shown of a delivery system 100 in accordance with various embodiments herein. As such, for example, the tunneling sheath 104 and the balloon catheter 106 can pass through the vessel 150 of a patient without being disposed within an introducing sheath. In some embodiments, the introducing sheath may have been removed. In other embodiments an introducing sheath is simply not used.

Referring now to FIG. 6, a schematic view is shown of a tunneling sheath in accordance with various embodiments herein. The tunneling sheath 104 can include a shaft 602, a proximal collar 105 and a distal end 107. In some embodiments, an annular tip 608 can be disposed on the distal end 107 of the tunneling sheath 104. The annular tip 608 can define a central aperture 606 which leads to the lumen of the tunneling sheath 104. The annular tip 608 can be formed of a material, such as a polymer, with a relatively soft durometer rating. By way of example, the material of the annular tip 608 can have a durometer rating in the range of about 30 to about 80. The annular tip can be formed of a material having a durometer rating that is different than the durometer rating of a material of the shaft.

Referring now to FIG. 7, a cross-sectional view of the shaft of a tunneling sheath is shown as taken along line 7-7' of FIG. 6. The shaft 602 can be formed of a polymer. Exemplary polymers can include, but are not limited to, polyurethane, PEBA (polyether block amide, e.g. VESTAMID E or PEBAX), polytetrafluoroethylene, fluorinated ethylene propylene (FEP), and polyamide (such as polyamide 12, NYLON), amongst others. Polymers herein can include homopolymers of the foregoing, blends including such polymers, and/or copolymers including portions of such polymers. In some embodiments, the wall of the shaft exhibits high kink resistance. The wall of the shaft 602 can be relatively thin. The wall of the shaft 602 can have a thickness of about 0.01 inch to about 0.1 inch. In various embodiments, a lubricious coating can be disposed on the inside of the tunneling sheath 104, the outside of the tunneling sheath 104, or on both the inside and the outside of the tunneling sheath 104. Exemplary polymers for lubricious coatings are described in greater detail below. The tunneling sheath can be of various lengths. In some embodiments, the tunneling sheath can be about 30 to about 70 centimeters. In some embodiments, the tunneling sheath can be about 40 to about 55 centimeters. In various embodiments, the tunneling sheath can be longer than an introducer sheath that is used for a procedure.

Figure 8:
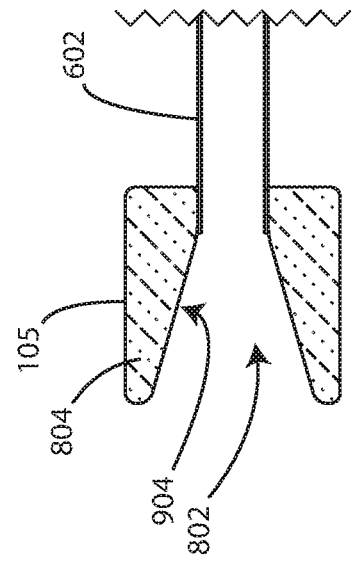
FIG. 8 is a schematic cross-sectional view of a proximal collar in accordance with various embodiments herein.

The proximal collars of the tunneling sheath 104 can have various configurations. Referring now to FIG. 8, a schematic cross-sectional view is shown of a proximal collar 105 in accordance with various embodiments herein. The proximal end of the shaft 602 can fit within at least a portion of the proximal collar 105. The proximal collar 105 can define a central lumen 802. The proximal collar 105 can be formed of a material 804. The proximal collar 105 can specifically be formed of a polymer. Exemplary polymers can include, but are not limited to, silicones (polysiloxanes), PEBA (polyether block amide, e.g. VESTAMID E or PEBAX), polytetrafluoroethylene, and fluorinated ethylene propylene (FEP), amongst others. Polymers herein can include homopolymers of the foregoing, blends including such polymers, and/or copolymers including portions of such polymers.

Figure 9:
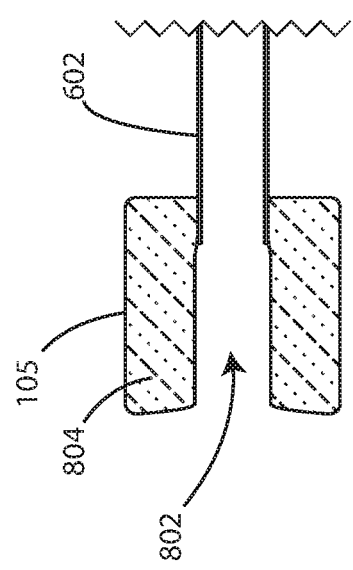
FIG. 9 is a schematic cross-sectional view of a proximal collar in accordance with various embodiments herein.

Some proximal collars can have differing configurations. Referring now to FIG. 9 is a schematic cross-sectional view is shown of a proximal collar in accordance with various embodiments herein. The proximal end of the shaft 602 can fit within at least a portion of the proximal collar 105. The proximal collar 105 can define a central lumen 802. In this embodiment, the central lumen 802 can include a taper 904, such that the lumen is wider at the proximal end than at the distal end.

Figure 10:
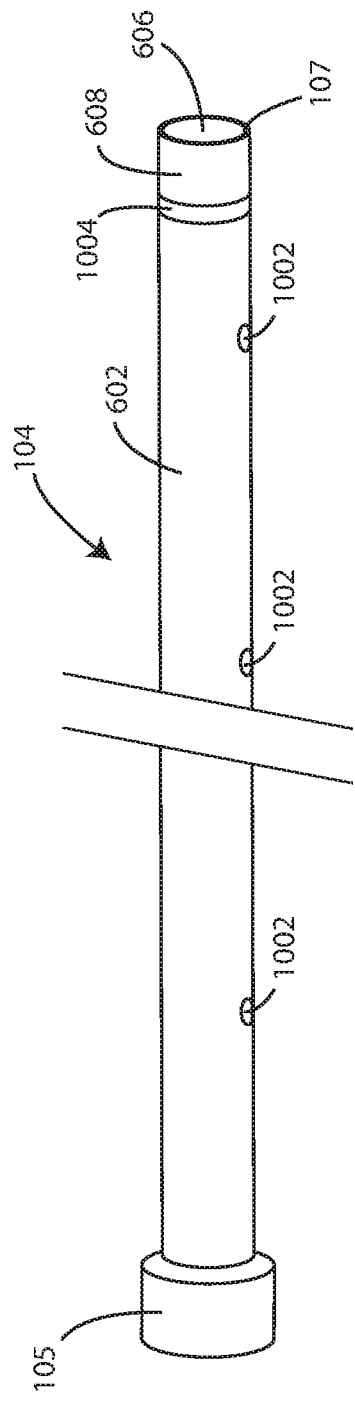
FIG. 10 is a schematic view of a tunneling sheath in accordance with various embodiments herein.

In some embodiments, the shaft of the tunneling sheath can include apertures (or vents or ports) along the lengthwise axis. Aperture or ports can be useful so as to provide for a way for fluid to enter or leave from the lumen of the tunneling sheath. Referring now to FIG. 10, a schematic view is shown of a tunneling sheath 104 in accordance with various embodiments herein. The tunneling sheath 104 can include a shaft 602, a proximal collar 105 and a distal end 107. In some embodiments, an annular tip 608 can be disposed on the distal end 107 of the tunneling sheath 104. The annular tip 608 can define a central aperture 606 which leads to the lumen of the tunneling sheath 104. A plurality of apertures 1002 can be disposed along the length of the shaft 602. In some embodiments, the tunneling sheath 104 can also include a radiopaque marker 1004 disposed on the tubular shaft adjacent to the distal end of the shaft 602. In some embodiments, the volume of the tubular shaft that is not taken up by the balloon catheter is filled with a fluid. In some embodiments, the fluid can be a biocompatible liquid.

Figure 11:
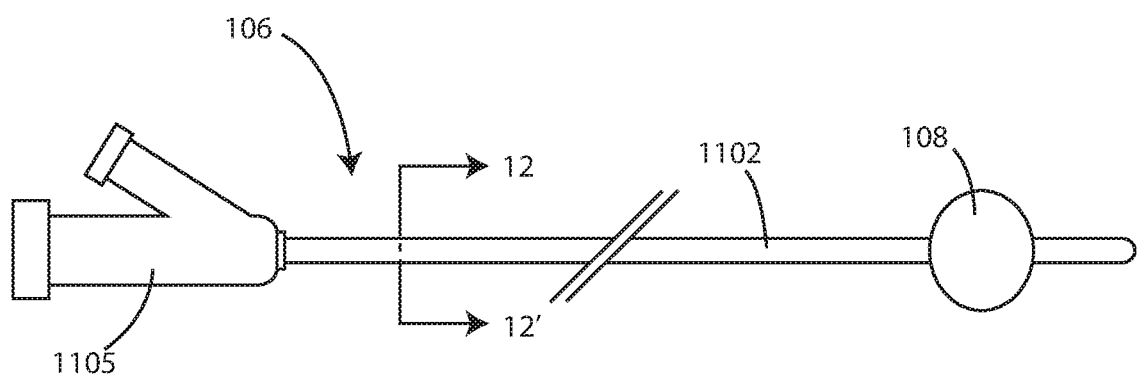
FIG. 11 is a schematic view of a balloon catheter in accordance with various embodiments herein.

Referring now to FIG. 11, a schematic view of a balloon catheter is shown in accordance with some embodiments herein. The balloon catheter 106 can be, for example, a drug eluting balloon catheter. Balloon catheter constructions are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. In some embodiments, the balloon catheter can also include a stent, scaffold, scoring device or the like.

Figure 12:
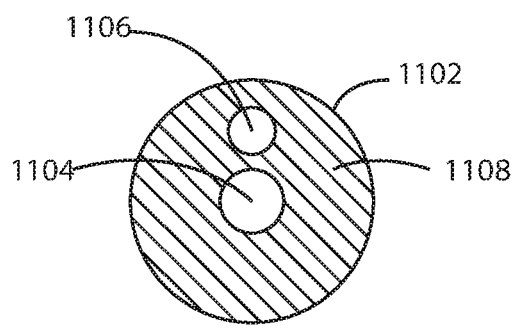
FIG. 12 is a schematic cross-sectional view of the balloon catheter as take along line 12-12' of FIG. 11.

The balloon catheter 106 includes a catheter shaft 1102 and a manifold end 1105. The balloon catheter 106 also includes an inflatable balloon 108 (or expandable balloon) disposed around the catheter shaft 1102. In FIG. 11, the balloon 108 is shown in an inflated configuration. The catheter shaft 1102 can include a channel to convey air through the catheter shaft 1102 and to or from the balloon 108, so that the balloon 108 can selectively go from a deflated configuration to the inflated configuration and back again. The catheter shaft, and/or the balloon, can have a coating, such as those described herein, disposed thereon. Referring now to FIG. 12, a cross-sectional view of a balloon catheter shaft is shown as taken along line 12-12' of FIG. 11. The catheter shaft 1102 can include a first lumen 1106, such as to convey a fluid to and from the balloon, and a second lumen 1104, such as to accommodate a guide wire passing there through. In various embodiments, the catheter shaft 1102 can include from 1 to 8 lumens or internal passageways therein. The catheter shaft 1102 can include a substrate 1108. The substrate 1108 can be formed of various materials including, but not limited to, polymers such as PET (polyethylene terephthalate), PEBA (polyether block amide, e.g. VESTAMID E or PEBAX), polyamides (such as polyamide 12, NYLON), polyesters, polyurethanes, polyolefins, styrenic block polymers, and the like. Polymers herein can include homopolymers of the foregoing, blends including such polymers, and/or copolymers including portions of such polymers.

In some embodiments, a method of delivering an active agent coated balloon into a subject is included. The method can include inserting a delivery system for introducing an active agent coated balloon into a subject. The balloon catheter can already be disposed within the tubular shaft of the tunneling sheath when the delivery system is introduced into a patient. In some cases, the balloon catheter can be pre-loaded into the tunneling sheath before being handled by a clinician, such as during a manufacturing process. In other embodiments, the balloon catheter can be loaded into the tunneling sheath (but before introduction into the patient) by the clinician at the time of use. In some embodiments, inserting a delivery system into a subject comprises inserting the delivery system into an introducer sheath.

The delivery system can include a tubular shaft having an outer diameter and defining a lumen, the shaft having a proximal end and a distal end. The delivery system can further include a proximal collar defining a lumen. The proximal collar can be attached to the tubular shaft at the proximal end. The proximal collar can have an outer diameter that is greater than the outer diameter of the tubular shaft. The delivery system can further include a balloon catheter comprising a balloon catheter shaft disposed within the tubular shaft, the balloon catheter shaft comprising a lumen for the passage of a fluid therein. The balloon catheter can further include an expandable balloon disposed on the balloon catheter shaft in fluid communication with the lumen of the balloon catheter shaft. An active agent layer can be disposed on the expandable balloon.

The method can further include advancing the delivery system through a blood vessel of the subject so as to be adjacent the site of an area to be treated. The position of the expandable balloon can be stationary relative to the tubular shaft as the delivery system is advanced through the blood vessel of the patient. The method can further include advancing the balloon catheter shaft and the expandable balloon out of the tubular shaft. The method can further include inflating the expandable balloon so that it contacts the area to be treated.

In some embodiments, the method can further include deflating the expandable balloon, moving the balloon catheter shaft and the expandable balloon back into the tubular shaft, and withdrawing the delivery system from the blood vessel of the patient. In some embodiments, the area to be treated can be a target lesion. In some embodiments, the method can further include engaging an attachment mechanism to keep the tubular shaft and the balloon catheter shaft static to one another as the delivery system is advanced through the blood vessel of the subject. In some embodiments, inserting a delivery system for introducing an active agent coated balloon into a subject further comprises inserting the delivery system through an introducer sheath (or a guide catheter or guide sheath, etc.). In some embodiments, inserting a delivery system for introducing an active agent coated balloon into a subject can be performed without the delivery system passing through an introducer sheath.

Portions of delivery systems herein can be covered with a coating. For example, hydrophilic polymeric coatings can be applied to portions of the delivery system to impart lubricity and decrease particulate shedding. In some examples, portions of the tunneling sheath can be coated with hydrophilic polymers to induce lubricity. For example, the inner and/or outer diameter of the shaft of the tunneling sheath can be coated with lubricious low friction coatings such as hydrophilic polymers to induce lubricity. In other examples, the outer diameter of the shaft of the balloon catheter can coated or lined with lubricious low friction coatings. Lubricious low friction coatings can be formed with friction reducing or lubricating materials such as silicone oil, perfluorinated oils or waxes or with covalently bonded coatings that impart lower friction, such as hydrophilic polymers described herein.

Exemplary embodiments of surfaces, including low-friction surfaces for the devices herein include substrates prepared from low friction materials (e.g. PTFE and PTFE liners) and surfaces that can be made to be low friction by addition of coatings (e.g. coatings with hydrophilic polymers).

One class of hydrophilic polymers useful as polymeric materials for hydrophilic coating formation can be synthetic hydrophilic polymers. Synthetic hydrophilic polymers that are biostable (i.e., that show no appreciable degradation in vivo) can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these. Examples of polymers that can be formed from these monomers include poly(acrylamide), poly(methacrylamide), poly(vinylpyrrolidone), poly(acrylic acid), poly(ethylene glycol), poly(vinyl alcohol), and poly (HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,Ndimethylacrylamide-co-aminopropylmethacrylamide) and poly(acrylamide-co-N,Ndimethylaminopropylmethacrylamide) are described in example 2 of U.S. Pat. No. 7,807,750 (Taton et al.), the disclosure of which is incorporated herein by reference.

Other hydrophilic polymers that can be useful in the present disclosure are derivatives of acrylamide polymers with photoreactive groups. One such representative hydrophilic polymer can be the copolymerization of N-[3-(4-benzoylbenzamido)propyl]methacrylamide (Formula I) with N-(3-aminopropyl)methacrylamide (Formula II) to produce the polymer poly(N-3-aminopropyl)methacrylamide-co-N-[3-(4-benzoylbenzamido)propyl]methacrylamide (Formula III). The preparation of the polymer is disclosed in Example 1 of US Patent Publication 2007/0032882 (to Lodhi, et al.), the full content of which is incorporated herein by reference.

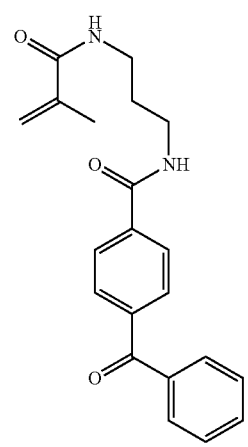

Formula I

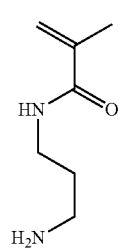

Formula II

Formula III

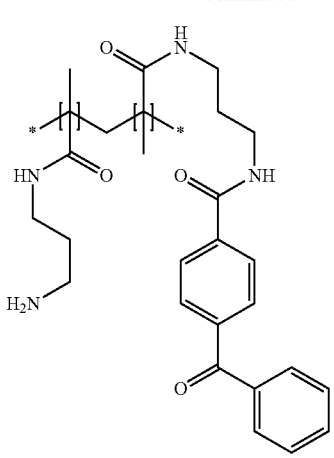

In some embodiments, the hydrophilic polymer can be a vinyl pyrrolidone polymer, or a vinyl pyrrolidone/(meth)acrylamide copolymer such as poly(vinylpyrrolidone-co-methacrylamide). If a PVP copolymer is used, it can be a copolymer of vinylpyrrolidone and a monomer selected from the group of acrylamide monomers. Exemplary acrylamide monomers include (meth)acrylamide and (meth)acrylamide derivatives, such as alkyl(meth)acrylamide, as exemplified by dimethylacrylamide, and aminoalkyl(meth)acrylamide, as exemplified by aminopropylmethacrylamide and dimethylaminopropylmethacrylamide. For example, poly(vinylpyrrolidone-co-N,N-dimethylaminopropylmethacrylamide) is described in example 2 of U.S. Pat. No. 7,807,750 (Taton et al.).

In one embodiment, the polymers and copolymers as described are derivatized with one or more photoactivatable group(s). Exemplary photoreactive groups that can be pendent from biostable hydrophilic polymer include aryl ketones, such as acetophenone, benzophenone, anthraquinone, anthrone, quinone, and anthrone-like heterocycles. Aryl ketones herein can specifically include diaryl ketones. Polymers herein can provide a hydrophilic polymer having a pendent activatable photogroup that can be applied to the expandable and collapsible structure, and can then treated with actinic radiation sufficient to activate the photogroups and cause covalent bonding to a target, such as the material of the expandable and collapsible structure. Use of photo-hydrophilic polymers can be used to provide a durable coating of a flexible hydrogel matrix, with the hydrophilic polymeric materials covalently bonded to the material of the expandable and collapsible structure.

A hydrophilic polymer having pendent photoreactive groups can be used to prepare the flexible hydrogel coating. Methods of preparing hydrophilic polymers having photoreactive groups are known in the art. For example, methods for the preparation of photo-PVP are described in U.S. Pat. No. 5,414,075, the disclosure of which is incorporated herein by reference. Hydrophilic photo-polyacrylamide polymers such as poly(acrylamide-co-N-(3-(4-benzoylbenzamido)propyl)methacrylamide), "Photo PA", and derivatives thereof can be used to form hydrophilic coatings in exemplary embodiments of the present disclosure. Methods for the preparation of photo-polyacrylamide are described in U.S. Pat. No. 6,007,833, the disclosure of which is incorporated by reference.

Other embodiments of hydrophilic coatings include derivatives of photo-polyacrylamide polymers incorporating additional reactive moieties. Some exemplary reactive moieties include N-oxysuccinimide and glycidyl methacrylate. Representative photo-polyacrylamide derivatives incorporating additional reactive moieties include poly(acrylamide-co-maleic-6-aminocaproic acid-N-oxysuccinimide-co-N-(3-(4-benzoylbenzamido)propyl)methacrylamide) and poly(acrylamide-co-(3-(4-benzoylbenzamido)propyl)methacrylamide)-co-glycidylmethacrylate. Additional photo-polyacrylamide polymers incorporating reactive moieties are described in U.S. Pat. No. 6,465,178 (to Chappa, et al.), U.S. Pat. No. 6,762,019 (to Swan, et al.) and U.S. Pat. No. 7,309,593 (to Ofstead, et al.), the disclosures of which are herein incorporated by reference.

Other embodiments of exemplary hydrophilic coatings that include derivatives of photo-polyacrylamide polymers incorporating additional reactive moieties can be found in U.S. Pat. No. 6,514,734 (to Clapper, et al.), the disclosure of which is incorporated herein by reference in its entirety.

In yet other embodiments, the hydrophilic coating can include derivatives of photo-polyacrylamide polymers incorporating charged moieties. Charged moieties include both positively and negatively charged species. Exemplary charged species include, but are not limited to, sulfonates, phosphates and quaternary amine derivatives. Some examples include the negatively charged species N-acetylated poly(acrylamide-co-sodium-2-acrylamido-2-methylpropanesulfonate-co-N-(3-(4-benzoylbenzamido)propyl)methacrylamide)-co-methoxy poly(ethylene glycol) monomethacrylate. Other negatively charged species that can be incorporated into the hydrophilic coating are described in U.S. Pat. No. 4,973,993, the disclosure of which is incorporated herein by reference in its entirety. Positively charged species can include poly(acrylamide-co-N-(3-(4-benzoylbenzamido)propyl)methacrylamide)-co-(3-(methacryloylamino)propyl)trimethylammonium chloride. Other positively charged species that can be incorporated into the hydrophilic coating are described in U.S. Pat. No. 5,858,653 (to Duran et al.), the disclosure of which is incorporated herein by reference in its entirety.

In another embodiment, the polymers and copolymers as described are derivatized with one or more polymerizable group(s). Polymers with pendent polymerizable groups are commonly referred to as macromers. The polymerizable group(s) can be present at the terminal portions (ends) of the polymeric strand or can be present along the length of the polymer. In one embodiment polymerizable groups are located randomly along the length of the polymer.

Exemplary hydrophilic polymer coatings can be prepared using polymer grafting techniques. Polymer grafting techniques can include applying a nonpolymeric grafting agent and monomers to a substrate surface then causing polymerization of the monomers on the substrate surface upon appropriate activation (for example, but not limited to, UV radiation) of the grafting agent. Grafting methods producing hydrophilic polymeric surfaces are exemplified in U.S. Pat. Nos. 7,348,055; 7,736,689 and 8,039,524 (all to Chappa et al.) the full disclosures of which are incorporated herein by reference.

Optionally, the coating can include a crosslinking agent. A crosslinking agent can promote the association of polymers in the coating, or the bonding of polymers to the coated surface. The choice of a particular crosslinking agent can depend on the ingredients of the coating composition.

Suitable crosslinking agents can include two or more activatable groups, which can react with the polymers in the composition. Suitable activatable groups can include photoreactive groups as described herein, like aryl ketones, such as acetophenone, benzophenone, anthraquinone, anthrone, quinone, and anthrone-like heterocycles. A crosslinking agent including a photoreactive group can be referred to as a photo-crosslinker or photoactivatable crosslinking agent. The photoactivatable crosslinking agent can be ionic, and can have good solubility in an aqueous composition. Thus, in some embodiments, at least one ionic photoactivatable crosslinking agent can be used to form the coating. The ionic crosslinking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable crosslinking agents include 4,5-bis(4-benzoylphenylmethyleneoxy) benzene-1, 3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis [2-(4-benzoylbenzyloxy)ethyl]-2-aminoethanesulfonic acid or salt, and the like. See U.S. Pat. No. 6,077,698 (Swan et al.), U.S. Pat. No. 6,278,018 (Swan), U.S. Pat. No. 6,603,040 (Swan) and U.S. Pat. No. 7,138,541 (Swan) the disclosures of which are incorporated herein by reference.

Other exemplary ionic photoactivatable crosslinking agents include ethylenebis(4-benzoylbenzyldimethylammonium) dibromide and hexamethylenebis(4-benzoylbenzyldimethylammonium) dibromide and the like. See U.S. Pat. No. 5,714,360 (Swan et al.) the disclosures of which are incorporated herein by reference.

In yet other embodiments, restrained multifunctional reagents with photoactivatable crosslinking groups can be used. In some examples these restrained multifunctional reagents include tetrakis (4-benzoylbenzyl ether) of pentaerthyritol and the tetrakis (4-benzoylbenzoate ester) of pentaerthyritol. See U.S. Pat. No. 5,414,075 (Swan et al.) and U.S. Pat. No. 5,637,460 (Swan et al.) the disclosures of which are incorporated herein by reference.

Additional crosslinking agents can include those having formula Photo1-LG-Photo2, wherein Photo1 and Photo2 independently represent at least one photoreactive group and LG represents a linking group comprising at least one silicon or at least one phosphorus atom, wherein the degradable linking agent comprises a covalent linkage between at least one photoreactive group and the linking group, wherein the covalent linkage between at least one photoreactive group and the linking group is interrupted by at least one heteroatom. See U.S. Pat. No. 8,889,760 (Kurdyumov, et al.), the disclosure of which is incorporated herein by reference. Further crosslinking agents can include those having a core molecule with one or more charged groups and one or more photoreactive groups covalently attached to the core molecule by one or more degradable linkers. See U.S. Publ. Pat. App. No. 2011/0144373 (Swan, et al.), the disclosure of which is incorporated herein by reference.

Crosslinking agents used in accordance with embodiments herein can include those with at least two photoreactive groups. Exemplary crosslinking agents are described in U.S. Pat. No. 8,889,760, the content of which is herein incorporated by reference in its entirety.

In some embodiments, the first and/or second crosslinking agent can have a molecular weight of less than about 1500 kDa. In some embodiments the crosslinking agent can have a molecular weight of less than about 1200, 1100, 1000, 900, 800, 700, 600, 500, or 400.

In some embodiments, at least one of the first and second crosslinking agents comprising a linking agent having formula Photo1-LG-Photo2, wherein Photo1 and Photo2, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In some embodiments, at least one of the first and second crosslinking agents comprising a linking agent having a formula selected from:

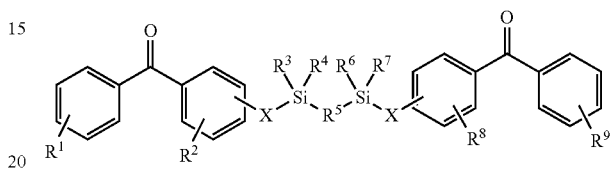

(a)

wherein R1, R2, R8 and R9 are any substitution; R3, R4, R6 and R7 are alkyl, aryl, or a combination thereof; R5 is any substitution; and each X, independently, is O, N, Se, S, or alkyl, or a combination thereof;

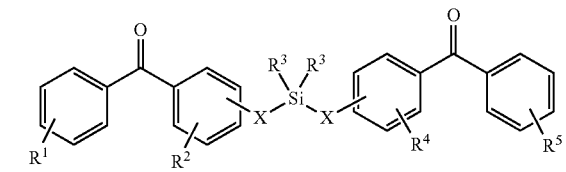

(b)

wherein R1 and R5 are any substitution; R2 and R4 can be any substitution, except OH; R3 can be alkyl, aryl, or a combination thereof; and X, independently, are O, N, Se, S, alkylene, or a combination thereof;

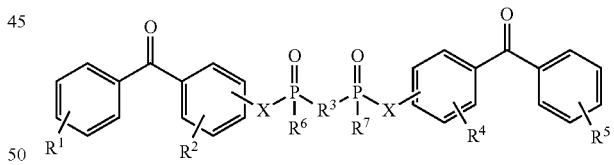

(c)

wherein R1, R2, R4 and R5 are any substitution; R3 is any substitution; R6 and R7 are alkyl, aryl, or a combination thereof; and each X can independently be O, N, Se, S, alkylene, or a combination thereof; and

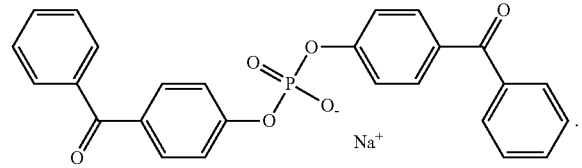

(d)

In a particular embodiment, the crosslinking agent can be bis(4-benzoylphenyl) phosphate.

In some embodiments, the photoactivatable crosslinking agent can be ionic, and can have good solubility in an aqueous composition, such as the first and/or second coating composition. Thus, in some embodiments, at least one ionic photoactivatable crosslinking agent is used to form the coating. In some cases, an ionic photoactivatable crosslinking agent can crosslink the polymers within the second coating layer which can also improve the durability of the coating.

Any suitable ionic photoactivatable crosslinking agent can be used. In some embodiments, the ionic photoactivatable crosslinking agent is a compound of formula I: X1-Y—X2 where Y is a radical containing at least one acidic group, basic group, or a salt of an acidic group or basic group. X1 and X2 are each independently a radical containing a latent photoreactive group. The photoreactive groups can be the same as those described herein. Spacers can also be part of X1 or X2 along with the latent photoreactive group. In some embodiments, the latent photoreactive group includes an aryl ketone or a quinone.

The radical Y in formula I provides the desired water solubility for the ionic photoactivatable crosslinking agent. The water solubility (at room temperature and optimal pH) is at least about 0.05 mg/ml. In some embodiments, the solubility is about 0.1 to about 10 mg/ml or about 1 to about 5 mg/ml.

In some embodiments of formula I, Y is a radical containing at least one acidic group or salt thereof. Such a photoactivatable crosslinking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic crosslinking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; X1 and X2 can contain photoreactive groups such as aryl ketones. Such compounds include 4,5-bis(4-benzoylphenylmethyleneoxy)benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate. For example, compounds of formula I can have a Y radical that contains an ammonium group; X1 and X2 can contain photoreactive groups that include aryl ketones. Such photoactivatable crosslinking agents include ethylenebis(4-benzoylbenzyldimethylammonium) salt; hexamethylenebis (4-benzoylbenzyldimethylammonium) salt; 1,4-bis(4-benzoylbenzyl)-1,4-dimethylpiperazinediium) salt, bis(4-benzoylbenzyl) hexamethylenetetraminediium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium] salt; and 1,1,4,4-tetrakis (4-benzoylbenzyl)piperzinediium salt. See U.S. Pat. No. 5,714,360. The counter ion is typically a carboxylate ion or a halide. On one embodiment, the halide is bromide.

In other embodiments, the ionic photoactivatable crosslinking agent can be a compound having the formula:

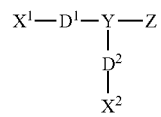

wherein X1 includes a first photoreactive group; X2 includes a second photoreactive group; Y includes a core molecule; Z includes at least one charged group; D1 includes a first degradable linker; and D2 includes a second degradable linker. Additional exemplary degradable ionic photoactivatable crosslinking agents are described in US Patent Application Publication US 2011/0144373 (Swan et al., "Water Soluble Degradable Crosslinker"), the disclosure of which is incorporated herein by reference.

In some aspects a non-ionic photoactivatable crosslinking agent can be used. In one embodiment, the non-ionic photoactivatable crosslinking agent has the formula XR1R2R3R4, where X is a chemical backbone, and R1, R2, R3, and R4 are radicals that include a latent photoreactive group. Exemplary non-ionic crosslinking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

In other embodiments, the non-ionic photoactivatable crosslinking agent can be represented by the formula:

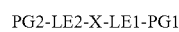

wherein PG1 and PG2 include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; LE1 and LE2 are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof. Other non-ionic crosslinking agents are described, for example, in U.S. application Ser. No. 13/316,030 filed Dec. 9, 2011 (Publ. No. US 2012/0149934) (Kurdyumov, "Photocrosslinker"), the disclosure of which is incorporated herein by reference.

Further embodiments of non-ionic photoactivatable crosslinking agents can include, for example, those described in US Pat. Publication 2013/0143056 (Swan et al., "Photo-Vinyl Primers/Crosslinkers"), the disclosure of which is incorporated herein by reference. Exemplary crosslinking agents can include non-ionic photoactivatable crosslinking agents having the general formula R1-X—R2, wherein R1 is a radical comprising a vinyl group, X is a radical comprising from about one to about twenty carbon atoms, and R2 is a radical comprising a photoreactive group.

A single photoactivatable crosslinking agent or any combination of photoactivatable crosslinking agents can be used in forming the coating. In some embodiments, at least one nonionic crosslinking agent such as tetrakis(4-benzoylbenzyl ether) of pentaerythritol can be used with at least one ionic crosslinking agent. For example, at least one non-ionic photoactivatable crosslinking agent can be used with at least one cationic photoactivatable crosslinking agent such as an ethylenebis(4-benzoylbenzyldimethylammonium) salt or at least one anionic photoactivatable crosslinking agent such as 4,5-bis(4-benzoyl-phenylmethyleneoxy)benzene-1,3-disulfonic acid or salt. In another example, at least one nonionic crosslinking agent can be used with at least one cationic crosslinking agent and at least one anionic crosslinking agent. In yet another example, a least one cationic crosslinking agent can be used with at least one anionic crosslinking agent but without a non-ionic crosslinking agent.

An exemplary crosslinking agent is disodium 4,5-bis[(4-benzoylbenzyl)oxy]-1,3-benzenedisulfonate (DBDS). This reagent can be prepared by combining 4,5-Dihydroxylbenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360, incorporated herein by reference).

Further crosslinking agents can include the crosslinking agents described in U.S. Publ. Pat. App. No. 2010/0274012 (to Guire et al.) and U.S. Pat. No. 7,772,393 (to Guire et al.) the content of all of which are herein incorporated by reference.

In some embodiments, crosslinking agents can include boron-containing linking agents including, but not limited to, the boron-containing linking agents disclosed in US Pat. Publication 2013/0302529 entitled "Boron-Containing Linking Agents" by Kurdyumov et al., the content of which is herein incorporated by reference. By way of example, linking agents can include borate, borazine, or boronate groups and coatings and devices that incorporate such linking agents, along with related methods. In an embodiment, the linking agent includes a compound having the structure (I):

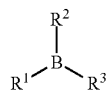

(I)

wherein R1 is a radical comprising a photoreactive group; R2 is selected from OH and a radical comprising a photoreactive group, an alkyl group and an aryl group; and R3 is selected from OH and a radical comprising a photoreactive group. In some embodiments the bonds B—R1, B—R2 and B—R3 can be chosen independently to be interrupted by a heteroatom, such as O, N, S, or mixtures thereof.

Additional agents for use with embodiments herein can include stilbene-based reactive compounds including, but not limited to, those disclosed in U.S. Pat. No. 8,487,137, entitled "Stilbene-Based Reactive Compounds, Polymeric Matrices Formed Therefrom, and Articles Visualizable by Fluorescence" by Kurdyumov et al., the content of which is herein incorporated by reference.

Additional photoreactive agents, crosslinking agents, hydrophilic coatings, and associated reagents are disclosed in U.S. Pat. No. 8,513,320 (to Rooijmans et al.); U.S. Pat. No. 8,809,411 (to Rooijmans); and 2010/0198168 (to Rooijmans), the content of all of which is herein incorporated by reference.

Natural polymers can also be used to form the hydrophilic coating. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

In some instances a tie layer can be used between the hydrophilic layer and the substrate. In yet other instances the tie layer can be added to the hydrophilic layer. The tie layer can act to increase the adhesion of the hydrophilic layer to the substrate. In other embodiments, the tie layer can act to increase adhesion of the hydrophobic active agent to the hydrophilic layer. Exemplary ties layers include, but are not limited to silane, butadiene, polyurethane and parylene. Silane tie layers are described in US Patent Publication 2012/0148852 (to Jelle, et al.), the content of which is herein incorporated by reference.

In exemplary embodiments, the hydrophilic layer can include tannic acid, polydopamine or other catechol containing materials.

In various embodiments, the active agent disposed on balloons herein includes one or more hydrophilic or hydrophobic active agents. In general, the term "hydrophobic active agent" refers to an active agent having solubility in water of less than about 100 µg/mL at 25° C. and neutral pH, less than about 10 µg/mL at 25° C. and neutral pH, or less than about 5 µg/ml at 25° C. and neutral pH. In various embodiments, the hydrophobic active agent is crystalline. In general, the term "crystalline" refers to a thermodynamically stable solid form of an active agent having "long range molecular order" in which the molecules are packed in a regularly ordered, repeating pattern. In another embodiment, the hydrophobic active agent is amorphous. The term "amorphous" refers to a solid form of an active agent in which the molecules do not have "long range molecular order", but rather are randomly arranged or retain only a "short range molecular order" typical of liquids.

The amount of hydrophobic active agent included in the active agent composition can vary depending upon many factors including the desired therapeutic outcome. However, compositions herein generally include at least about 1 mg/ml, 2 mg/ml, 3 mg/ml, 4 mg/ml, 5 mg/ml, or 10 mg/ml, 15 mg/ml, 20 mg/ml, or 25 mg/ml or up to about 25 mg/ml, 50 mg/ml, 75 mg/ml, 100 mg/ml, 125 mg/ml or 150 mg/ml hydrophobic active agent.

It will be appreciated that hydrophobic active agents can include agents having many different types of activities. In some embodiments, hydrophobic active agents can include, but are not limited to, antiproliferatives such as paclitaxel, sirolimus (rapamycin), everolimus, biolimus A9, zotarolimus, tacrolimus, and pimecrolimus and mixtures thereof; analgesics and anti-inflammatory agents such as aloxiprin, auranofin, azapropazone, benorylate, diflunisal, etodolac, fenbufen, fenoprofen calcium, flurbiprofen, ibuprofen, indomethacin, ketoprofen, meclofenamic acid, mefenamic acid, nabumetone, naproxen, oxyphenbutazone, phenylbutazone, piroxicam, sulindac; anti-arrhythmic agents such as amiodarone HCl, disopyramide, flecainide acetate, quinidine sulphate; anti-bacterial agents such as benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim; anti-coagulants such as dicoumarol, dipyridamole, nicoumalone, phenindione; anti-hypertensive agents such as amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL; anti-muscarinic agents: atropine, benzhexol HCl, biperiden, ethopropazine HCl, hyoscyamine, mepenzolate bromide, oxyphencylcimine HCl, tropicamide; anti-neoplastic agents and immunosuppressants such as aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone; beta-blockers such as acebutolol, alprenolol, atenolol, labetalol, metoprolol, nadolol, oxprenolol, pindolol, propranolol; cardiac inotropic agents such as amrinone, digitoxin, digoxin, enoximone, lanatoside C, medigoxin; corticosteroids such as beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone; lipid regulating agents such as bezafibrate, clofibrate, fenofibrate, gemfibrozil, probucol; nitrates and other anti-anginal agents such as amyl nitrate, glyceryl trinitrate, isosorbide dinitrate, isosorbide mononitrate, pentaerythritol tetranitrate.

Other hydrophobic active agents include, but are not limited to, active agents for treatment of hypertension (HTN), such as guanethidine.

In a particular embodiment, the hydrophobic active agent includes paclitaxel, sirolimus (rapamycin), everolimus, biolimus A9, zotarolimus, tacrolimus, and pimecrolimus and mixtures thereof.

In some embodiments, the hydrophobic active agent includes chemotherapeutics, exemplified by the family of fluorouracils (e.g. 4-FU and 5-FU) and carmustine (bischloroethylnitrosourea; BCNU).

In various embodiments, the hydrophobic active agent is combined with a cationic delivery agent in solution. In various embodiments, the hydrophobic active agent is combined with a cationic delivery agent to form a suspension. In another embodiment, solid hydrophobic active agent, amorphous or crystalline, is combined with pure or neat cationic delivery agent, amorphous or crystalline, to form a mixture. In other embodiments, the hydrophobic active agents is conjugated to a cationic delivery agent. The conjugation can include a hydrophobic active agent covalently bonded to the cationic delivery agent. In some embodiments wherein the hydrophobic agent is conjugated to the cationic delivery agent a linking agent can be used to attach the hydrophobic agent to the cationic delivery agent. Suitable linking agents include, but are not limited to, polyethylene glycol, polyethylene oxide and polypeptides of naturally-occurring and non-naturally occurring amino acids. In some embodiments, linking agents can be biodegradable or cleavable in vivo to assist in release of the hydrophobic active agents. Exemplary linking agents can further include alkane or aromatic compounds with heteroatom-substitutions such as N, S, Si, Se or O.

In various embodiments, the active agent composition in the active agent layer includes a hydrophobic active agent and cationic delivery agent. While not wishing to be bound by theory, it is believed that the charge provided by the cationic delivery agents results in the composition being electrostatically attracted to negative charges and/or polar groups associated with the lipid bilayer present on or in a tissues or organs of a patient or charged/polar groups associated with the extracellular matrix (e.g., collagen, fibronectin, laminin, etc.). Consequently, combining an active agent, particularly a hydrophobic active agent with a cationic delivery agent in a composition for local administration can help retain the hydrophobic active agent near the site of administration. It is also thought that the cationic delivery agent may increase tissue permeability, thereby enhancing uptake of the active agent by the target tissue and/or organ.

Cationic delivery agents can specifically include cationic lipids and net neutral lipids that have a cationic group. Exemplary lipids can include, but are not limited to, 3β-[N—(N',N'-dimethylaminoethane)-carbamoyl]cholesterol hydrochloride (DC-cholesterol); 1,2-dioleoyl-3-trimethylammonium-propane (DOTAP); dimethyldioctadecylammonium (DDAB); 1,2-dioleoyl-sn-glycero-3-ethylphosphocholine (EPC); 1,2-di-O-octadecenyl-3-trimethylammonium propane (DOTMA); 1,2-di-(9Z-octadecenoyl)-3-dimethylammonium-propane (DODAP); 1,2-dilinoleyloxy-3-dimethylaminopropane (DLinDMA) and derivatives thereof. Additional lipids can include, but are not limited to, 1,2-dioleoyl-sn-glycero-3-phosphoethanolamine (DOPE); cholesterol; 1,2-dioctadecanoyl-sn-glycero-3-phosphocholine (DSPC); 1,2-distearoyl-sn-glycero-3-phosphoethanolamine (DSPE).

Cationic delivery agents can specifically include cationic polymers. Cationic delivery agents can also include polycation-containing cyclodextrin, histones, protamines, cationized human serum albumin, aminopolysaccharides such as chitosan, peptides such as poly-L-lysine, poly-L-ornithine, and poly(4-hydroxy-L-proline ester, and polyamines such as polyethylenimine (PEI; available from Sigma Aldrich), polypropylenimine, polyamidoamine dendrimers (PAMAM; available from Sigma Aldrich), cationic polyoxazoline, polyvinylamine (PVAm), and poly(beta-aminoesters). Cationic delivery agents can also specifically include cationic lipidoids (as described by K. T. Love in the publication PNAS 107, 1864-1869 (2010)). Other exemplary cationic polymers include, but are not limited to, block copolymers such as PEG-PEI and PLGA-PEI copolymers.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A delivery system for introducing an active agent coated balloon into a subject comprising:
   a tunneling sheath comprising
      a tubular shaft having an outer diameter and defining a lumen, the tubular shaft having a proximal end and a distal end;
      a proximal collar defining a lumen, the proximal collar attached to the tubular shaft at the proximal end, the proximal collar comprising an outer diameter that is greater than the outer diameter of the tubular shaft; and
   a balloon catheter comprising
      a balloon catheter shaft disposed within the tubular shaft, the balloon catheter shaft comprising a lumen for the passage of a fluid therein;
      an expandable balloon disposed on the balloon catheter shaft in fluid communication with the lumen of the balloon catheter shaft; and
      an active agent layer disposed on the expandable balloon;
   an introducing sheath disposed about the tunneling sheath;
   wherein the position of the expandable balloon is configured to be stationary relative to the tubular shaft with the proximal collar of the tunneling sheath fastened onto the balloon catheter as the delivery system is passed through a blood vessel of a patient;
   wherein the expandable balloon is configured be passed at least part way out of the tubular shaft after the proximal collar of the tunneling sheath is unfastened from the balloon catheter; and
   wherein a volume of the tubular shaft that is not taken up by the balloon catheter is filled with a liquid as the expandable balloon is passed at least part way out of the tubular shaft.

2. The delivery system of claim 1, further comprising a radiopaque marker disposed on the tubular shaft adjacent to the distal end.

3. The delivery system of claim 1, further comprising a lubricious coating disposed on the luminal and abluminal surfaces of the tubular shaft.

4. The delivery system of claim 3, the lubricious coating comprising a photoactive reagent.

5. The delivery system of claim 1, the tubular shaft comprising polyurethane, polyether block amide, polytetrafluoroethylene, fluorinated ethylene propylene, and polyamide.

6. The delivery system of claim 1, the proximal collar comprising silicone, polyether block amide, and polytetrafluoroethylene.

7. The delivery system of claim 1, further comprising an annular tip attached to the distal end of the tubular shaft, the annular tip comprising a material having a durometer rating that is different than the durometer rating of a material of the shaft.

8. The delivery system of claim 1, wherein the lumen of the proximal collar is tapered.

9. The delivery system of claim 1, wherein the lumen of the proximal collar tapers from a first diameter adjacent the proximal end of the delivery system to a second diameter farther away from the proximal end of the delivery system, the second diameter less than the first diameter.

10. The delivery system of claim 1, the active agent layer comprising a bioactive agent for treating restenosis.

11. The delivery system of claim 10, the bioactive agent selected from the group consisting of paclitaxel, rapamycin and derivatives thereof.

12. The delivery system of claim 1, the liquid comprising biocompatible liquid.

13. The delivery system of claim 1, the tubular shaft comprising one or more apertures along the length of the tubular shaft other than at the proximal and distal ends, the one or more apertures providing fluid communication between the luminal and abluminal sides of the tubular shaft.

14. A method of delivering an active agent coated balloon into a subject comprising:
   inserting a delivery system for introducing an active agent coated balloon into a subject, the delivery system comprising
      a tunneling sheath comprising a tubular shaft having an outer diameter and defining a lumen, the tubular shaft having a proximal end and a distal end;
      a proximal collar defining a lumen, the proximal collar attached to the tubular shaft at the proximal end, the proximal collar comprising an outer diameter that is greater than the outer diameter of the tubular shaft;
      a balloon catheter comprising
         a balloon catheter shaft disposed within the tubular shaft, the balloon catheter shaft comprising a lumen for the passage of a fluid therein;
         an expandable balloon disposed on the balloon catheter shaft in fluid communication with the lumen of the balloon catheter shaft;
         an active agent layer disposed on the expandable balloon;
   fastening the proximal collar of the tunneling sheath onto the balloon catheter;
   advancing the delivery system through a blood vessel of the subject so as to be adjacent the site of an area to be treated, wherein the position of the expandable balloon is stationary relative to the tubular shaft as the delivery system is advanced through the blood vessel of the patient;
   unfastening the proximal collar of the tunneling sheath from the balloon catheter;
   advancing the balloon catheter shaft and the expandable balloon at least part way out of the tubular shaft; and
   inflating the expandable balloon so that it contacts the area to be treated; and
   wherein inserting a delivery system for introducing an active agent coated balloon into a subject further comprises inserting the delivery system through an introducer sheath configured to be disposed about the tubular shaft of the tunneling sheath.

15. The method of claim 14, further comprising:
   deflating the expandable balloon;
   moving the balloon catheter shaft and the expandable balloon back into the tubular shaft; and
   withdrawing the delivery system from the blood vessel of the patient.

16. The method of claim 14, the area to be treated comprising a lesion.

17. The method of claim 14, further comprising an attachment mechanism to keep the tubular shaft and the balloon catheter shaft static to one another as the delivery system is advanced through the blood vessel of the subject.

\* \* \* \* \*